US006649051B1

(12) United States Patent
Jamalabadi et al.

(10) Patent No.: US 6,649,051 B1
(45) Date of Patent: Nov. 18, 2003

(54) PROCESSING OF CHEMICALS IN FLOW-THROUGH DEVICE WITH POROUS MEDIA

(75) Inventors: Shahnaz Ghassemi Jamalabadi, Charlottesville, VA (US); Peter C. Rahn, Palmyra, VA (US); Kelvin Hammond, Charlottesville, VA (US); Omar Mneimne, Charlottesville, VA (US); Jeffrey A. Horsman, Charlottesville, VA (US)

(73) Assignee: Biotage, Inc., Charlottesville, VA (US)

( * ) Notice: Subject to any disclaimer, the term of this patent is extended or adjusted under 35 U.S.C. 154(b) by 0 days.

(21) Appl. No.: 10/136,131

(22) Filed: May 1, 2002

(51) Int. Cl.$^7$ ................................................ B01D 15/08
(52) U.S. Cl. ..................... 210/198.2; 210/243; 210/656; 210/748; 422/70
(58) Field of Search .................. 210/635, 656, 210/659, 198.2, 232, 238, 243, 282; 96/101, 105, 106; 422/70

(56) References Cited

U.S. PATENT DOCUMENTS 4,204,423 A * 5/1980 Jordan ....................... 73/23.25
5,549,819 A * 8/1996 Nickerson ................. 210/198.2
6,139,733 A 10/2000 Hargro et al. ............. 210/198.2
6,416,716 B1 * 7/2002 Shukla et al. ................ 422/101
6,423,120 B1 * 7/2002 Nickerson et al. .............. 95/87
6,530,260 B1 * 3/2003 Mustacich et al. .......... 73/23.41
6,541,272 B1 * 4/2003 Mitra .......................... 436/178
2003/0109053 A1 * 6/2003 Stone .......................... 436/161

OTHER PUBLICATIONS

Information from Personal Chemistry website www.personalchemistry.com undated pp. 1–6.
Information from CEM website www.CEM.com undated pp. 1–15.
Information from Milestone Inc. Website www.milestonesci.com/SYN%Features.htm pp. 1–14 Aug. 30, 2002.

* cited by examiner

Primary Examiner—Ernest G. Therkorn
(74) Attorney, Agent, or Firm—Fish & Richardson P.C.

(57) ABSTRACT

A method of processing a sample comprising introducing a sample into a flow-through device containing a porous solid media therein, and thereafter subjecting the device to microwave energy. Also disclosed is a flow through device including solid porous media therein and attached active components.

26 Claims, 2 Drawing Sheets

US 6,649,051 B1

PROCESSING OF CHEMICALS IN FLOW-THROUGH DEVICE WITH POROUS MEDIA

TECHNICAL FIELD

The invention relates to processing of chemicals in flow-through devices with porous media.

U.S. Pat. No. 6,139,733, which is hereby incorporated by reference, describes a sample module made of a flow-through device that contains porous media and describes adding a chemical sample to the module prior to connecting the module to (or inserting the module into) a chromatography column. The sample can be added to the module in a dissolution solvent that can be removed by vacuum or heat prior to connection to the chromatography column.

SUMMARY

In one aspect, the invention features, in general, processing a chemical sample by introducing a sample into a flow-through device containing a porous solid media therein, and thereafter subjecting the device to microwave energy.

In another aspect, the invention features, in general, introducing a chemical sample into a flow-through device containing a porous solid media therein and active components attached to the solid media, and thereafter subjecting the device to energy in order to accelerate reactions implemented by the active components, the reactions resulting in a reaction product created from the sample.

In another aspect, the invention features, in general, introducing reagents into a flow-through device containing a porous solid media therein and active components attached to the solid media, causing a synthesis reaction involving the reagents in the flow-through device and resulting in a reaction product, thereafter placing the flow-through device into an entrance region within a chromatography column, and thereafter carrying out chromatography on the reaction product.

In another aspect, the invention features, in general a chromatography sample module including a flow-through member having walls and having an inlet end and an outlet end; a solid porous media disposed within the flow-through member and including attached active components, the media being spaced from the inlet end so that the walls extend above the media and so that the flow-through member defines a receiving region adapted to receive a head piece; and a sample carried on the media.

In another aspect, the invention features, in general, a tubular member that is sized to fit entirely within the end of a chromatography column containing a separation media, the module having an inlet and an outlet, and solid porous media within the tubular member and spaced from the inlet, so that the tubular member defines a receiving region adapted to receive a head piece. The tubular member is sized to be sealed within the chromatography column with a sealing device used to seal the chromatography column. The solid porous media includes attached active components and carries a sample.

In another aspect, the invention features, in general a flow-through device having walls and having an inlet end and an outlet end; a solid porous media disposed within the flow-through device including attached active components, the media being spaced from the inlet end so that the walls extend above the media and so that the flow-through member defines a receiving region adapted to receive a head piece; and a sample carried on the media.

Particular embodiments of the invention may include one or more of the following features. In particular embodiments, the sample is introduced into the flow-through device in a solvent that is evaporated by microwave energy prior to carrying out chromatography. In some embodiments, the solid media includes active components attached thereto, and the microwave energy speeds up the reactions involving the active components. In some embodiments the sample includes reagents that undergo a chemical reaction to form a reaction product. The active components attached to the solid media can include scavengers to remove excess reagents. The scavengers can be electrophile scavengers, e.g., amino scavengers, $TsNHNH_2$ scavengers, or SH scavengers. The scavengers can be nucleophile scavengers, e.g., TsCl scavengers and NCO scavengers. The scavengers can be base scavengers, e.g., a quaternary amine scavenger. The scavengers can be acid scavengers, e.g., TsOH scavengers or COOH scavengers. The active components can be coupling agents, e.g., DCC coupling agents, HOBt coupling agents, or NHS coupling agents. The active components can be a catalyst, e.g., TsOH. The active components can be a catalyst remover, e.g., DEAM.

Embodiments of the invention may include one or more of the following advantages. The use of microwave energy to evaporate solvent in a flow-through device in which a sample carried in a solvent has been absorbed onto solid media in the flow through device greatly speeds up and simplifies the evaporation process. Attaching active components to the solid media in a flow-through device that can be used to introduce a sample into a chromatography column, permits the same device to be used as a reaction chamber and sample introduction device, simplifying and speeding up synthesis and purification. Subjecting the device with solid media and attached active components to microwave or other energy speeds up the synthesis or other reactions therein.

Other features and advantages of the invention will be apparent from the following detailed description and from the claims.

DETAILED DESCRIPTION

Figure 1:
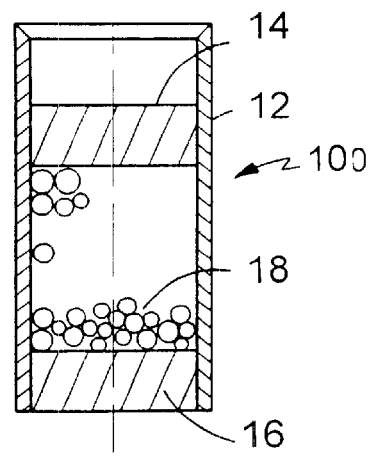
FIG. 1 is a diagrammatic vertical sectional view of a flow-through device with a porous media therein.

Referring to FIG. 1, there is shown flow-through device 10, which includes cylindrical tube 12, porous plates 14, 16 (made of inert plastic porous frits or glass or Teflon), and porous solid media 18 (only partially shown in the figures) between porous plates 14, 16. Tube 12 can be made from glass, polyethylene, polypropylene, Teflon and other plastics. Media 18 can take various forms depending on the application. Media 18 can be silica, other conventional chromatography media, or solid media that has attached active components such as scavengers, coupling agents, catalysts, or catalyst removers.

Figure 2:
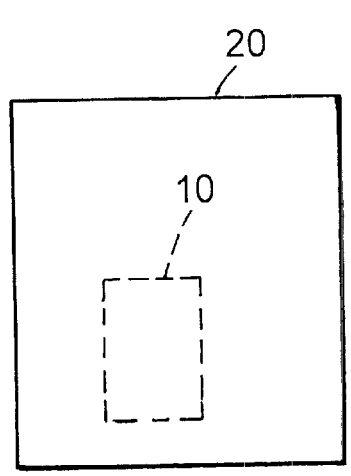
FIG. 2 is a diagrammatic view showing processing a sample in the FIG. 1 device in a microwave chamber.

Referring to FIG. 2, flow-through device 10, containing a sample to be processed therein, is shown being subjected to microwave energy in microwave chamber 20. In some applications, the processing involves removal of a dissolution solvent in which a sample compound of interest is dissolved. In other applications, the media plays an active role in chemical reactions taking place in the flow-through device. In some applications a conventional microwave oven can be used as the microwave chamber. In some other applications, it is better to use a microwave chamber with more precise controls, e.g., units available from Personal Chemistry, CEM or Milestone, Inc. (Monroe, Conn.).

Use of Flow-through Device 10 for Removal of Dissolution Solvent

As is described in the above-referenced patent, when chemists optimize liquid chromatographic separations conditions, they may need to dissolve the sample mixture in a dissolution solvent which may be nonideal for elution. This can result in poor separation and poor recovery of desired components in a chromatography column. For example, polar solvents such as methanol, isopropanol (IPA), acetone, and ethylacetate (EtOAc) can interfere with chromatographic purification. The above-referenced patent describes adding a sample dissolved in a dissolution solvent to the top of the flow-through device (referred to as a sample module in the patent), where it is drawn into the media by capillary action. The sample absorbs onto the media, and the dissolution solvent is then removed by placing the flow-through device in a vacuum chamber and/or applying heat prior to placing the device in, or otherwise connecting it to, a chromatography column.

In order to avoid the use of a vacuum chamber or heat and to accelerate the drying of the solvent, one can instead subject the sample to microwave energy in microwave chamber 20. For example, subjecting flow through devices available from Biotage under the Flash 12 trade designation and containing one ml of the solvents IPA, EtOAc, acetone, methanol, and dichloromethane (DCM) in a conventional microwave oven (power set at 30) for 60 seconds resulted in the following percentage evaporations respectively, 82%, 72%, 96%, 88% and 92%. In general, removal of 80% of the polar solvent eliminates the interference of the chromatographic separation. When one is using the microwave chamber and sample module solely for the purpose of removing a dissolution solvent prior to chromatography, one may wish to use an inert media (e.g., sea sand or diatomaceous earth) instead of silica, in order to minimize the possibility of hydrolyzing acid sensitive groups. When polar solvent is removed, sample retention is enhanced, compound resolution is improved and tighter elution bands result. There also are increased separation efficiencies, lower volume fractions and increased loading capacities.

Figure 3:
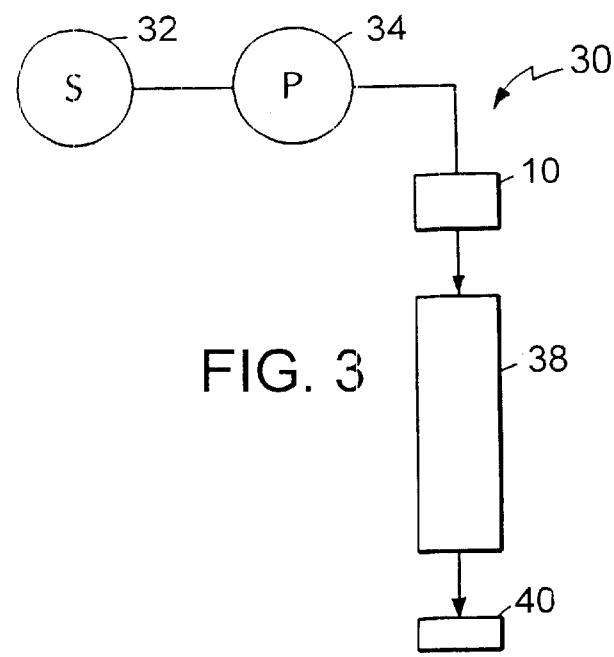
FIG. 3 is a schematic diagram of showing subsequent use of the FIG. 1 device in a chromatography system.
Figure 4:
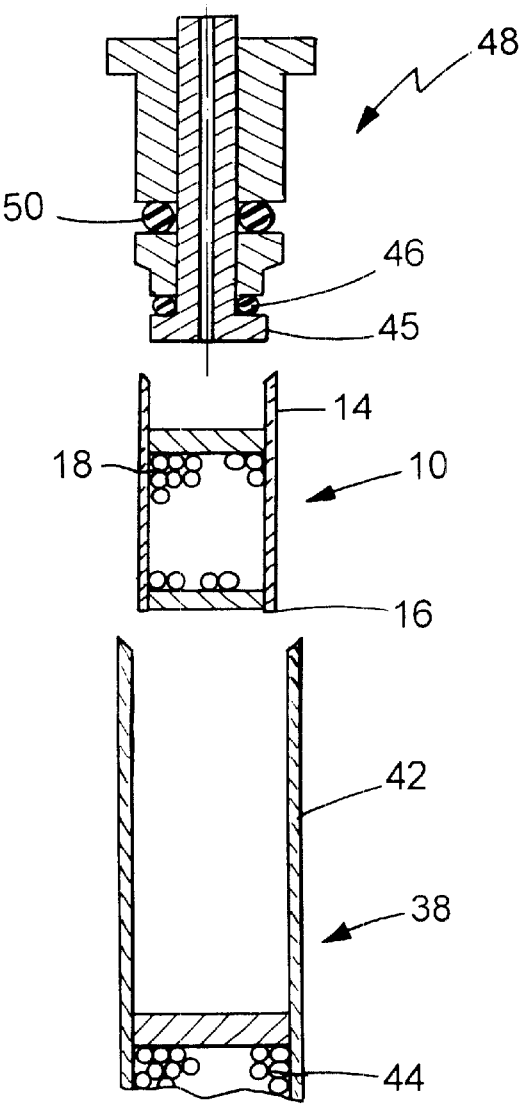
FIG. 4 shows how the FIG. 1 device fits within a chromatography column of the FIG. 3 chromatography system.

Referring to FIG. 3, flow-through device 10 (with a preabsorbed sample therein) is used in chromatography system 30, which also includes a source of solvent 32 (different than the polar dissolution solvent), pump 34, liquid chromatography column 38, and sample fraction collection system 40. In this system, solvent from source 32 is pumped by pump 34 through flow-through device 10 and chromatography column 38, carrying sample from device 10 thereto, to perform the chromatographic separation of the sample. FIG. 4 shows how flow-through device 10 is sized to fit entirely within the end 42 of chromatography column 38 containing a separation media 44. In device 10, the upper plate 14 is spaced from the upper end so that tubular member 12 defines a receiving region adapted to receive the lower end 45 and the lower compressible sealing ring 46 of sealing head piece 48, which also has an upper compressible sealing ring 50 for providing a seal to the chromatography column 38.

Use of Flow-Through Device 10 as a Reaction Chamber

Flow-through device 10 can also be used as a reaction chamber in which the solid media includes attached active components such as scavengers, coupling agents, catalysts, or catalyst removers that assist in a chemical reaction therein. In this application, device 10 serves as a reaction chamber for solid phase organic synthesis (SPOS) or solid-assisted synthesis (SAS). In typical SPOS, a desired product (e.g., a small organic molecule being created as part of a combinatorial library) is synthesized on a bed; reactants and excess reagent stay in solution, and, at the end of the synthesis process, the excess reagents are washed out. In typical SAS, solid supports are used to hold reagents, catalysts for synthesis or chemoselective scavengers used to remove excess reactants during purification; this approach when applied to solution phase typically requires a long time for completion and involves many manual steps including washing and extractions.

Figure 5:
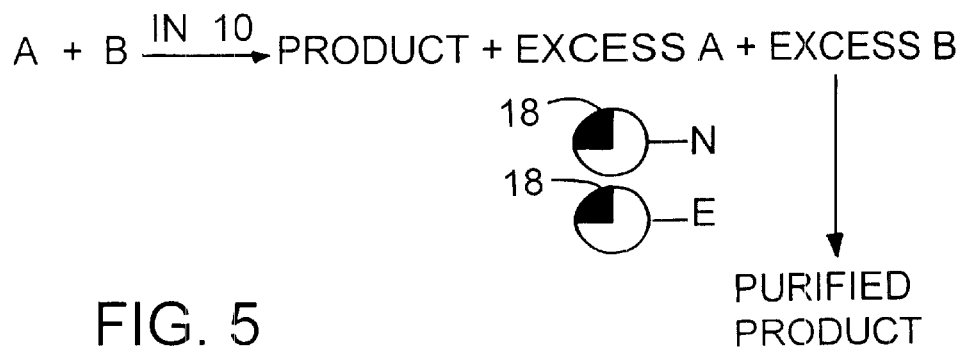
FIG. 5 illustrates reactions that can take place in the FIG. 1 device when it is used as a reaction device.

An example in which device 10 is used to facilitate scavenging of excess reagents is shown in FIG. 5. In this example, reagent A and reagent B are introduced into a flow-through device 10 that includes solid media 18 with attached nucleophile scavengers N and attached electrophile scavengers E. Reagents A and B combine to form the Product, and excess reagent A and excess reagent B are removed by the scavengers, resulting in a Purified Product, which is removed from device 10 in liquid form. The reaction can take place at room temperature or be aided by application of microwave energy (in microwave chamber 20 in FIG. 2) or conventional heat (e.g., from a hot plate) or a UV lamp. The use of microwave energy is superior because it results in an extremely short reaction time.

In a reaction arrangement where, following synthesis, the desired product is purified in a chromatography column, flow-through device 10 provides for ease of introduction of the sample into the chromatography column as described in the above-referenced patent. Where it is desired to remove solvent prior to purification in the chromatography column, microwave energy can also be used to provide fast solvent evaporation. By using microwave synthesis on chemical samples and/or reagents in flow-through device 10 (with or without microwave drying) and then directly connecting device 10 to chromatography column 38 for separation and purification, one can potentially synthesize and purify new compounds in less than one hour.

Examples of nucleophile scavengers N are TsCl scavengers and NCO scavengers. These scavengers can be used to remove excess nucleophiles including amine, hydrazine, alcohols and organometallics.

Examples of electrophile scavengers are amino scavengers, $TsNHNH_2$ scavengers, and SH scavengers. The amino scavengers can scavenge acid chloride, sulfonylchloride and isocyanates. The $TsNHNH_2$ scavengers can scavenge aldehydes and ketones. The SH scavengers can scavenge alkylating agents, ranging from octyl bromide to benzyl bromide. Other electrophile and nucleophile scavengers can be used.

In addition, base scavengers, e.g., quaternary amine, can be used as a general base to quench reactions, neutralize amine hydrochlorides or to scavenge a variety of acidic molecules like carboxylic acids or acidic phenols.

Also, acid scavengers, e.g., TsOH and COOH, can be used. E.g., solid media with attached TsOH can be used as an equivalent to the strong cation-exchange resin, Amberlyst A-15 (Rohm & Hass). The device 10 with TsOH attached to the solid media can be used for removal of basic compounds, e.g., primary, secondary and tertiary amine, by quaternary salt formation. Also it can be used for quenching reactions with aqueous or soluble organic acids and for Boc-deblocking by catch and release of amine derivatives.

Coupling agents, such as DCC, HOBt and NHS, can also be attached to solid media and used for the synthesis of amides and esters.

A catalyst, e.g., TsOH can also be attached to a solid media and used as a catalyst for esterification.

A catalyst remover can also be attached. E.g., DEAM attached to a solid media is highly efficient in sacavenging oxopilic inorganic and organometallic complexes, including those of boron, titanium and tin. This resin can be used to quench reactions and remove metallic reagents, catalysts or byproducts.

The reactions involving the various scavengers, coupling agents, catalysts and catalyst removers can be speeded up by placing the device 10 with the indicated solid media and reagents in microwave chamber 20 and applying microwave energy. In addition, the efficiencies of the reactions are improved such that the amount of excess reagents needed can be reduced.

Use of flow-through device 10 as described can eliminate the manual manipulation involved in cleaning up a sample through extractions and washing and also provides a convenient reaction vessel.

Other embodiments of the invention are within the scope of the appended claims.

What is claimed is:

1. A chromatography apparatus comprising
   a chromatography sample module comprising
      a flow-through member having an inlet and an outlet, and
      a media within said flow-through member, said media being spaced from said inlet, so that said flow-through member defines a receiving region adapted to receiving a head piece for making a seal with said flow-through member,
      said media including attached active components;
      a sample on said media,
      said sample including reagents that undergo a chemical reaction to form a reaction product through exposure to energy from an energy source; and
      a radiation energy source for emitting radiation energy.

2. The chromatography apparatus of claim 1, wherein said media is prepacked within said flow-through member.

3. The chromatography apparatus of claim 1, wherein said sample has been dissolved in a solution, and dried, resulting in a dried sample on said media.

4. The chromatography apparatus of claim 1, wherein said radiation energy source emits microwave radiation.

5. The chromatography apparatus of claim 1, wherein said radiation energy source emits UV radiation.

6. The chromatography apparatus of claim 1, wherein said radiation energy source is capable of heating at least a portion of said sample.

7. The chromatography apparatus of claim 1, wherein said media includes scavengers attached to said media.

8. The chromatography apparatus of claim 7, wherein said scavengers are electrophile scavengers.

9. The chromatography apparatus of claim 8, wherein said electrophile scavengers are selected from the group consisting of amino scavengers, $TsNHNH_2$ scavengers, and SH scavengers.

10. The chromatography apparatus of claim 7, wherein said scavengers are nucleophile scavengers.

11. The chromatography apparatus of claim 10, wherein said nucleophile scavengers are selected from the group consisting of TsCl scavengers and NCO scavengers.

12. The chromatography apparatus of claim 7, wherein said scavengers are base scavengers.

13. The chromatography apparatus of claim 12, wherein said base scavenger is a quaternary amine scavenger.

14. The chromatography apparatus of claim 7, wherein said scavengers are acid scavengers.

15. The chromatography apparatus of claim 14, wherein said acid scavengers are selected from the group consisting of TsOH scavengers and COOH scavengers.

16. The chromatography apparatus of claim 1 wherein said media includes coupling agents attached to said media.

17. The chromatography apparatus of claim 16, wherein said coupling agents are selected from the group consisting of DCC coupling agents, HOBt coupling agents, and NHS coupling agents.

18. The chromatography apparatus of claim 1, wherein said media includes a catalyst attached to said media.

19. The chromatography apparatus of claim 18, wherein said catalyst is TsOH.

20. The chromatography apparatus of claim 1, wherein said media includes a catalyst remover attached to said media.

21. The chromatography apparatus of claim 20, wherein said catalyst remover is DEAM.

22. The chromatography apparatus of claim 1, wherein said flow-through member is sized to fit entirely within the end of a chromatography column containing a second media.

23. The chromatography apparatus of claim 1, wherein said reagents can undergo a synthesis reaction to form said reaction product.

24. A chromatography apparatus comprising
   a chromatography sample module comprising a tubular member that is sized to fit entirely within the end of a chromatography column containing a separation media carrying a sample, said module having an inlet and an outlet, and chromatography media within said tubular member and spaced from said inlet, so that said tubular member defines a receiving region adapted to receive a head piece, said tubular member sized to be sealed within said chromatography column with a sealing device used to seal said chromatography column,
   said chromatography media including attached active components;
   a sample on said chromatography media,
   said sample including reagents that undergo a chemical reaction to form a reaction product through exposure to energy from an energy source; and
   a radiation energy source for emitting radiation energy.

25. A chromatography apparatus comprising
   a chromatography sample module comprising
      a flow-through member having walls and having an inlet end and an outlet end;
      a media disposed within said flow-through member, said media being spaced from said inlet end so that said walls extend above said media and so that said flow-through member defines a receiving region adapted to receive a head piece;
      a sample carried on said media,
      said media including attached active components,
      said sample including reagents that undergo a chemical reaction to form a reaction product through exposure to energy from an energy source; and
      a radiation energy source for emitting radiation energy.

26. The chromatography apparatus of claims 1, 24, or 25 wherein said active components are at least one member selected from the group consisting of scavengers, coupling agents, catalysts, and catalyst removers.

* * * * *